United States Patent
Ocel et al.

(10) Patent No.: US 9,962,130 B1
(45) Date of Patent: *May 8, 2018

(54) STRETCHER COMPATIBLE WITH MRI ENTRY SYSTEMS

(71) Applicants: Gregory J. Ocel, Brainerd, MN (US); Beth M. Lacy, Baxter, MN (US); Kenneth L. Lacy, Baxter, MN (US)

(72) Inventors: Gregory J. Ocel, Brainerd, MN (US); Beth M. Lacy, Baxter, MN (US); Kenneth L. Lacy, Baxter, MN (US)

( * ) Notice: Subject to any disclaimer, the term of this patent is extended or adjusted under 35 U.S.C. 154(b) by 101 days.

This patent is subject to a terminal disclaimer.

(21) Appl. No.: 14/845,287

(22) Filed: Sep. 4, 2015

Related U.S. Application Data

(63) Continuation of application No. 14/074,397, filed on Nov. 7, 2013, now Pat. No. 9,144,409.

(51) Int. Cl.
| | | |
|---|---|---|
| *A61B 6/04* | (2006.01) | |
| *A61G 1/02* | (2006.01) | |
| *A61B 5/055* | (2006.01) | |
| *A61G 1/04* | (2006.01) | |
| *A61G 7/05* | (2006.01) | |
| *B60B 33/00* | (2006.01) | |

(52) U.S. Cl.
CPC .......... *A61B 6/0442* (2013.01); *A61B 5/0555* (2013.01); *A61G 1/02* (2013.01); *A61G 1/0287* (2013.01); *A61G 1/04* (2013.01); *A61G 7/0507* (2013.01); *B60B 33/0078* (2013.01)

(58) Field of Classification Search
CPC .......... A61G 1/02; A61G 1/04; A61G 1/0237; A61G 1/0287; A61G 7/0507; A61B 6/0407; A61B 6/0442; A61B 5/0555; B60B 33/00; B60B 33/0078
See application file for complete search history.

(56) References Cited

U.S. PATENT DOCUMENTS

| | | | | |
|---|---|---|---|---|
| 3,304,116 A | * | 2/1967 | Stryker | A61G 7/00 296/20 |
| 3,493,085 A | * | 2/1970 | Libhart | B60B 33/0078 16/35 R |
| 3,838,687 A | * | 10/1974 | Mosher | A61B 6/045 128/200.11 |
| 4,349,937 A | * | 9/1982 | Fontana | B60B 33/0078 16/35 R |
| 4,559,668 A | * | 12/1985 | Black | B60B 33/0078 16/21 |

(Continued)

*Primary Examiner* — Nicholas F Polito
*Assistant Examiner* — David R Hare
(74) *Attorney, Agent, or Firm* — Albert W. Watkins

(57) ABSTRACT

An MRI compatible stretcher has a plurality of non-magnetically susceptible and electrically conductive metal members in physically overlapping sections, each having electrically non-conductive spacers separating the overlapping sections to prevent electrical conductivity there between. The insulators break electrical conductivity and thereby prevent the formation of large and continuous metal current loops, while the overlap ensures continuous metal strength and integrity. In particular embodiments, flanges terminate longitudinally extensive metal members, and the electrically non-conductive spacers separate the flanges from adjacent metal members. Fasteners secure the flanges, spacers and adjacent metal members together.

17 Claims, 6 Drawing Sheets

(56) References Cited

U.S. PATENT DOCUMENTS

| | | | | |
|---|---|---|---|---|
| 4,567,894 A * | 2/1986 | Bergman | ............... | A61B 5/0555 |
| | | | | 403/325 |
| 4,584,989 A * | 4/1986 | Stith | ................... | A61G 7/00 |
| | | | | 128/870 |
| 4,768,241 A * | 9/1988 | Beney | ................... | A61G 7/00 |
| | | | | 5/503.1 |
| 4,835,815 A * | 6/1989 | Mellwig | ............ | B60B 33/0078 |
| | | | | 16/35 R |
| 5,111,541 A * | 5/1992 | Wagner | ............... | A61B 5/0555 |
| | | | | 5/131 |
| 5,191,675 A * | 3/1993 | Ishikura | ............ | B60B 33/0078 |
| | | | | 16/35 R |
| 5,236,066 A * | 8/1993 | O'Neal | ............... | B60B 33/0078 |
| | | | | 16/35 R |
| 5,283,919 A * | 2/1994 | Grant | ................... | A61G 1/013 |
| | | | | 5/176.1 |
| 5,335,651 A * | 8/1994 | Foster | .................. | A61G 7/00 |
| | | | | 128/202.13 |
| 5,499,415 A * | 3/1996 | McKenna | ............ | A61B 6/032 |
| | | | | 378/209 |
| 5,570,483 A * | 11/1996 | Williamson | ......... | A61G 1/0293 |
| | | | | 177/144 |
| 6,330,926 B1 * | 12/2001 | Heimbrock | ............ | A61G 7/018 |
| | | | | 180/65.1 |
| 6,640,364 B1 * | 11/2003 | Josephson | ............ | A61B 6/0457 |
| | | | | 378/209 |
| 6,725,501 B2 * | 4/2004 | Harris | ................. | B60B 33/0007 |
| | | | | 16/31 A |
| 6,735,794 B1 * | 5/2004 | Way | .................... | A61G 1/0293 |
| | | | | 16/35 R |
| 7,490,377 B2 * | 2/2009 | Ahlman | ............... | A61B 6/0442 |
| | | | | 5/613 |
| 7,913,337 B1 * | 3/2011 | Masson | ................... | A61G 7/16 |
| | | | | 5/503.1 |
| 7,926,145 B2 * | 4/2011 | Liao | ................... | B60B 33/0018 |
| | | | | 16/18 R |
| 8,100,307 B2 * | 1/2012 | Chinn | ..................... | A61G 1/04 |
| | | | | 211/74 |
| 9,144,409 B1 * | 9/2015 | Ocel | ..................... | A61B 6/0442 |
| 2004/0034935 A1 * | 2/2004 | Ferneau | ................. | A61G 1/0567 |
| | | | | 5/618 |
| 2011/0272200 A1 * | 11/2011 | Clapp | ................... | A61G 1/017 |
| | | | | 180/54.1 |
| 2013/0340167 A1 * | 12/2013 | Karwal | ................ | A61G 7/005 |
| | | | | 5/611 |

* cited by examiner

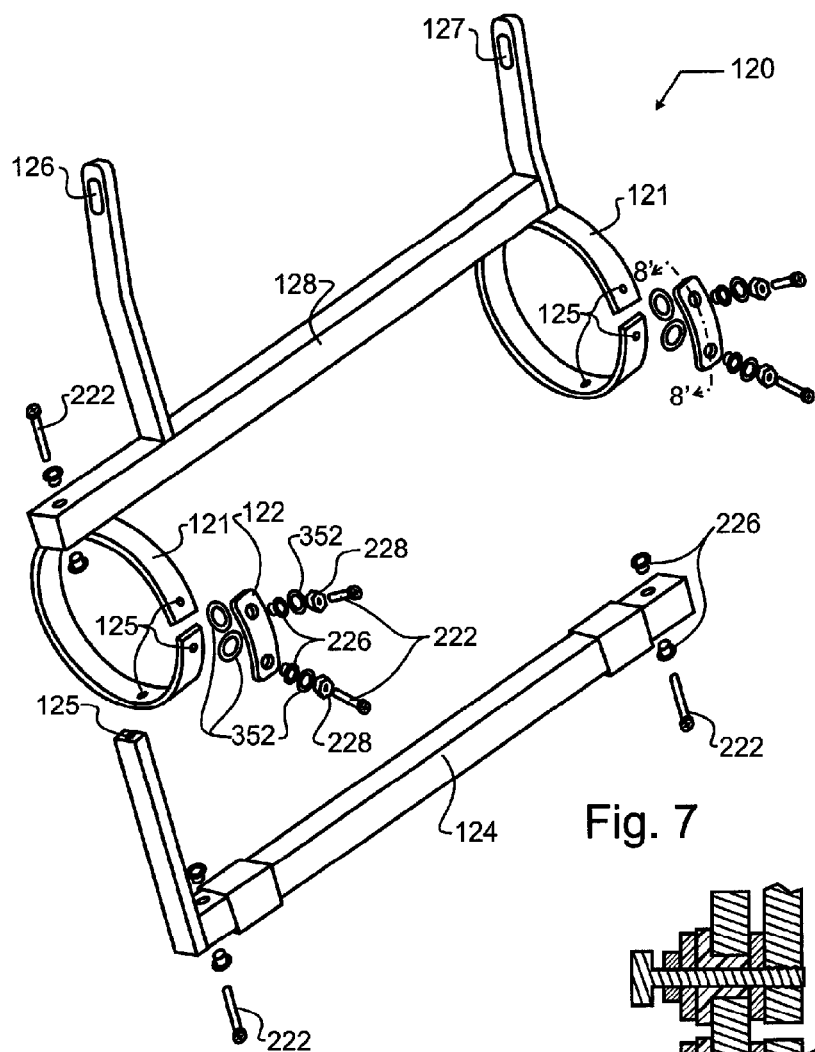
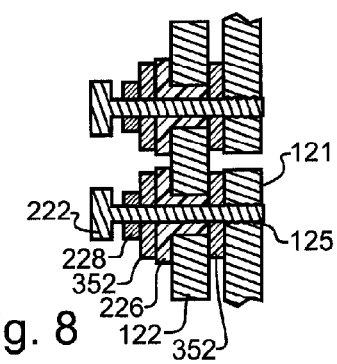
Fig. 7
Fig. 8

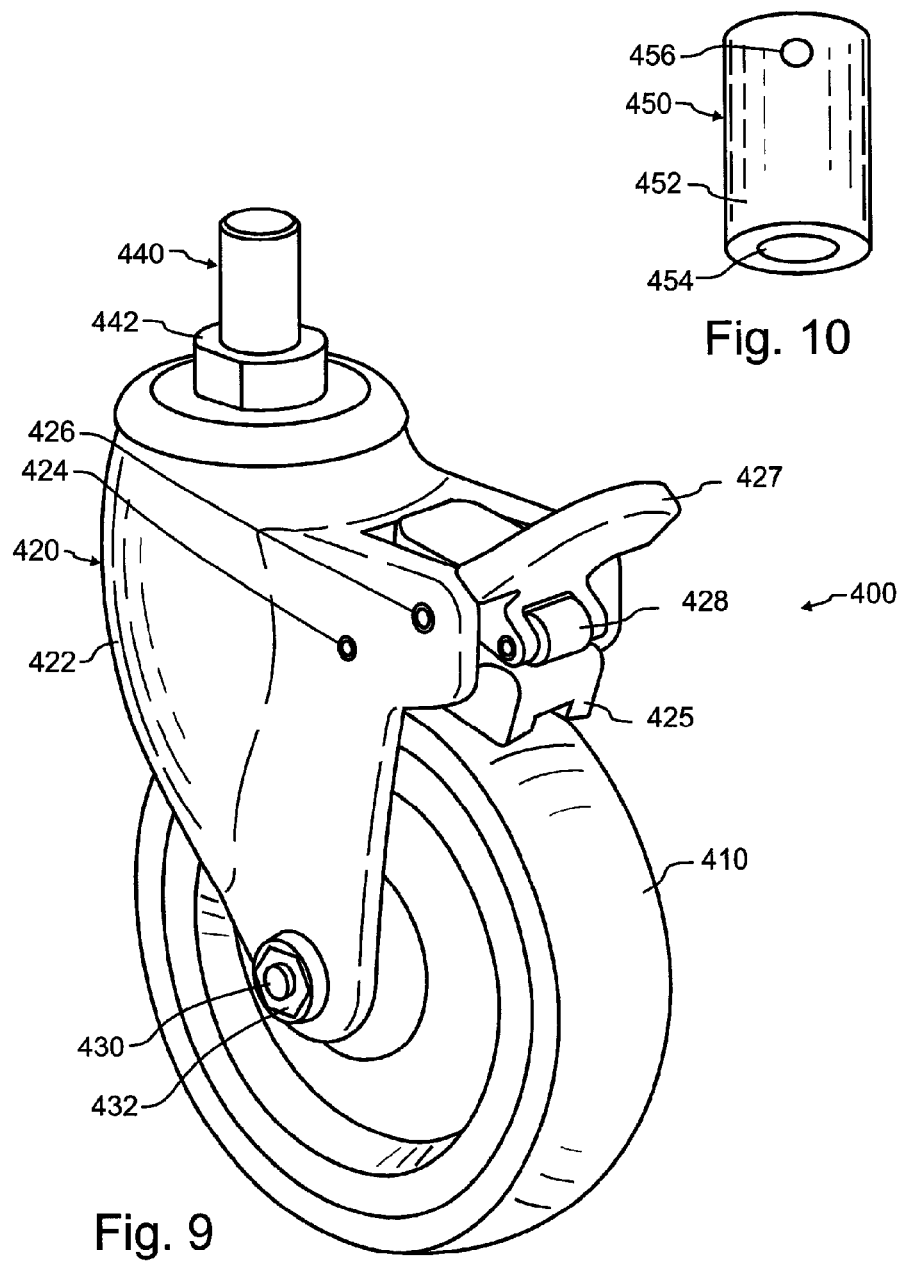

STRETCHER COMPATIBLE WITH MRI ENTRY SYSTEMS

CROSS REFERENCE TO RELATED APPLICATIONS

The present application is a continuation of U.S. Ser. No. 14/074,397 filed Nov. 7, 2013 of like title and inventorship, the entire contents which are incorporated herein by reference.

BACKGROUND OF THE INVENTION

1. Field of the Invention

The present invention pertains generally to beds, and more particularly to beds for relocating a person, commonly referred to as a gurney or stretcher. The stretcher may further include a hoisting, lifting, elevating, or raising device and wheels for free traveling. Most particularly, the present invention pertains to such gurneys that are compatible for use with magnetic imaging systems such as MRI and NMR systems commonly found within a health care facility.

2. Description of the Related Art

Throughout the ages, medical practitioners were limited by what they could detect with their senses. Visual inspection of a patient might reveal a joint dislocation or exterior wounds, a sore throat indicative of a disease or infection, or even a color indicative of a condition such as jaundice. Combining information derived from other senses, such as lymph node swelling identified through tactile palpitations, could confirm the diagnosis of a disease or infection. Sounds were amplified with stethoscopes, and a practitioner might detect an unusual odor or smell, such as sweet or foul smells. While much less common, even taste was used, such as to detect a salty sweat consistent with cystic fibrosis. In spite of the centuries of refinement, these diagnostic techniques lacked the ability to give the physician access to the interior of the human body, without harming, hindering or seriously disrupting a person.

A little more than a century ago, with the discovery of x-rays and the refinement of photographic film technology, medical practitioners could for the first time noninvasively view internal body features. This drastically improved a physician's ability to accurately diagnose and treat diseases and injuries, and has become a mainstay of medical practice. While x-rays are very effective in viewing density variations, such as the shape and size of a bone fracture or a tissue mass, they do little in distinguishing the type or biological activity of the tissues.

Much more recently, Magnetic Resonance Imaging (MRI) machines, which may also be referred to as Nuclear Magnetic Resonance (NMR) or Magnetic Resonance Tomography (MRT) machines, have been developed that complement the capabilities of x-ray machines. MRI machines develop contrasting images of various soft tissues of the body. This is done without the need for harmful ionizing radiation of x-ray equipment. As a result, modern MRI machines are very common in health care facilities, and are used extensively for medical diagnostics.

As an essential part of proper operation, MRI machines create an extremely strong magnetic field. This magnetic field can undesirably turn common articles made from materials such as iron and steel into dangerous projectiles that can harm patients, medical personnel, and the machines themselves. In addition to human danger and mechanical damage, the result of an accident involving these vital diagnostic machines will often also include shutting down the machine for an extended period of time. Since these machines are typically very expensive, there is rarely excess capacity available. Even short-term shut-down of a machine can lead to costly and life-endangering delays in diagnosing and treating patients. For smaller facilities that rely upon a single machine, this can be particularly critical, since the loss of the diagnostic capability of these machines at an inopportune moment can literally lead to further loss of life. Consequently, much care must be taken to avoid bringing magnetic objects into the vicinity of the strong magnetic field.

While many magnetic objects are visually identifiable, this is not always the case. Some materials are very hard to visually distinguish. In addition, while most modern surgical implants have been designed to be non-magnetic in consideration for the common use of this diagnostic equipment, an occasional patient may unknowingly have either a very old implant or through traumatic injury have a foreign object within their body that is magnetically susceptible. These magnetic objects can cause harm to the patient and equipment, particularly where such objects are relatively large or in troublesome locations within the patient.

Even medical personnel who have been educated about the hazards of MRI machines and who are familiar with the risk of magnetic materials will sometimes forget or otherwise fail to recognize that a particular object is magnetic. In other instances, an emergency may arise and the medical personnel may not have time to consciously consider whether an item or piece of equipment needed for the emergency is magnetic.

While normally considered less dramatic and consequential than magnetic objects flying towards an MRI machine, the presence of small magnetic objects can also disrupt the proper operation of the MRI equipment. MRI machines depend not only upon very strong magnetic fields, but also upon very consistent fields. Unfortunately, even quite small magnetically susceptible materials tend to distort the field undesirably, and so can consequentially degrade the images produced.

In consideration of the foregoing, most MRI facilities are designed with limited and controlled access. This will commonly include a magnetic material detection station, such as a screening portal, through which all patients, medical and service personnel must pass. The magnetic material detection station is generally sufficiently separated from the machine to allow safe detection and correction. For example, if a building repair person unknowingly carrying a steel hammer were to pass through a screening portal, the portal would signal the presence of the hammer in time to allow the building repair person to discard the hammer. The repair person would the pass through the screening portal a second time prior to entering the MRI room to confirm that no other magnetic objects were present. In this manner, the screening portal acts as a vital safeguard and reminder.

Exemplary screening apparatus are described in the following U.S. patents and published patent applications, the teachings and contents which are incorporated herein by reference: U.S. Pat. No. 6,956,369 by Czipott et al, entitled "Screening method and apparatus"; U.S. Pat. No. 7,106,056 by Czipott et al, entitled "Security screening method and apparatus"; U.S. Pat. No. 7,154,266 by Czipott et al, entitled "Screening method and apparatus"; U.S. Pat. No. 7,239,134 by McClure et al, entitled "Screening method and apparatus"; U.S. Pat. No. 7,315,166 by Czipott et al, entitled "Magnetic resonance imaging screening method and apparatus"; U.S. Pat. No. 8,035,377 by Czipott et al, entitled "Method for excluding magnetic objects from magnetic resonance imaging facility"; 2008/0281187 by Massengill et al, entitled "Ferromagnetic threat detection method apparatus"; and U.S. Pat. No. 8,115,480 by Masubuchi et al, entitled "Magnetic body detector".

Within most medical facilities, patients are transported upon gurneys that are fabricated from a steel framework. Many smaller components such as fasteners, casters, and auxiliary components are also commonly fabricated from steel. Steel components used in the fabrication of gurneys are generally of relatively lower cost to fabricate than other components, while providing excellent strength to weight ratios. A steel surface is quite hard and scuff and scratch resistant, and is easily cleaned and sanitized. Furthermore, the condition of steel components can often be ascertained from a simple visual inspection. Consequently, gurneys have been preferentially fabricated from steel for centuries. Unfortunately, steel is magnetic, and so is incompatible with magnetic imaging equipment.

Another common gurney material is plastic. In contrast to metals, over time and particularly when under load, plastic components tend to sag or flow. Imminent failures tend to be harder to detect. Furthermore, the plastic surfaces are softer than metal counterparts, and so are more easily scuffed or roughened. Cleaning and sanitization can be more difficult and complex, and the gurneys may require more frequent replacement.

While some satisfactory gurneys exist that are made entirely from non-metallic materials, it remains desirable to fabricate a gurney from metal components where possible, while avoiding undesirable triggering of screening portals. Since most screening portals used with MRI machines are designed to detect magnetically susceptible materials such as steel and iron, some individuals have tried to fabricate gurneys from non-magnetically susceptible materials. Aluminum, for example, is not magnetically susceptible.

Some alloys of stainless steel are also either not magnetically susceptible, or are drastically less so than steel. As a result, these materials are generally safe to use in the vicinity of MRI machinery. Some gurneys have been fabricated from stainless steel alloys. Depending upon the composition, these alloys may form austenite, which is not ferromagnetic. However, austenite is paramagnetic in nature, and so is still attracted to an externally applied magnetic field, albeit less forcefully than ferromagnetic materials such as steel, martensite alloys and ferrite.

Many MRI screening portals use electromagnetic fields to detect paramagnetic and ferromagnetic materials. These electromagnetic fields can induce electrical current in electrically conductive materials such as aluminum and stainless steel. Unfortunately, induced electrical currents in turn generate magnetic fields, which means that many screening portals cannot adequately distinguish the electrically conductive gurney materials such as austenite stainless steel and aluminum from ferromagnetic gurney materials. As a result, these prior art attempts to fabricate non-magnetic metallic gurneys have failed to gain wide acceptance due to undesirable triggering of screening portal alarms.

A variety of patents and published applications that illustrate various gurneys and patient transport systems, the teachings and contents which are incorporated herein by reference, include: U.S. Pat. No. 5,111,541 by Wagner, entitled "Non-metallic gurney for patient transport"; FR 2,789,302 by Antar; U.S. Pat. No. 6,640,364 by Josephson et al, entitled "Pedestal for use with patient transport system for multiple imaging systems"; U.S. Pat. No. 7,216,383 by Heinl et al, entitled "Support device for a patient"; U.S. Pat. No. 8,132,276 by Klemm et al, entitled "Patient support apparatus"; U.S. Pat. No. 7,490,377 by Ahlman, entitled "Patient single surface system"; U.S. Pat. No. 7,784,121 by Ahlman, entitled "Patient single surface system"; and U.S. Pat. No. 8,046,851 by Ahlman, entitled "Patient single surface system". In addition to the foregoing patents, Webster's New Universal Unabridged Dictionary, Second Edition copyright 1983, is incorporated herein by reference in entirety for the definitions of words and terms used herein.

SUMMARY OF THE INVENTION

In one manifestation, the invention is an MRI compatible stretcher comprising a plurality of non-magnetically susceptible and electrically conductive metal members in physically overlapping sections. Electrically non-conductive spacers separate the overlapping sections to prevent electrical conductivity therebetween. Flanges may also terminate longitudinally extensive metal members, and in such case the electrically non-conductive spacers separate the flanges from adjacent metal members. Fasteners secure the flanges, spacers and adjacent metal members together.

OBJECTS OF THE INVENTION

A first object of the invention is to fabricate a gurney primarily from non-magnetically susceptible metal components that provide excellent strength to weight ratios, and a surface that is hard and scuff and scratch resistant and is easily cleaned and sanitized. A second object of the invention is to fabricate a gurney that is safe to use in the vicinity of MRI machinery. Another object of the present invention is that the primarily metal gurney be divided into relatively small electrically conductive sections that do not falsely trigger common MRI screening portals. A further object of the invention is to accomplish the foregoing objectives while providing a gurney which may still be readily manufactured and assembled, without undue complexity or cost.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which:

FIG. 7 illustrates a preferred embodiment oxygen tank holder used in the preferred embodiment MRI compatible stretcher of FIG. 1 from an isometric projected and partially exploded view.

FIG. 8 illustrates an electrically insulating and mechanically sound coupling used in the preferred embodiment oxygen tank holder of FIG. 7 from a sectional view taken along section line 8' in FIG. 7.

FIG. 9 illustrates a preferred embodiment wheel used in the preferred embodiment MRI compatible stretcher of FIG. 1 from an isometric projected view.

FIG. 10 illustrates a preferred embodiment wheel adapter used in the preferred embodiment MRI compatible stretcher of FIG. 1 from an isometric projected view.

DESCRIPTION OF THE PREFERRED EMBODIMENT

Manifested in the preferred embodiment MRI compatible stretcher 100, the present invention provides non-magnetically susceptible metal such as aluminum in physically overlapping sections, but with electrically non-conductive spacers separating the overlapping sections. The insulators break electrical conductivity and thereby prevent the formation of large and continuous metal current loops. An MRI compatible stretcher 100 properly designed in accord with the teachings of the present invention will incorporate these electrically insulating and mechanically sound couplings in every component that would otherwise present a large enough current loop to falsely trigger the MRI screening portal.

Figure 1:
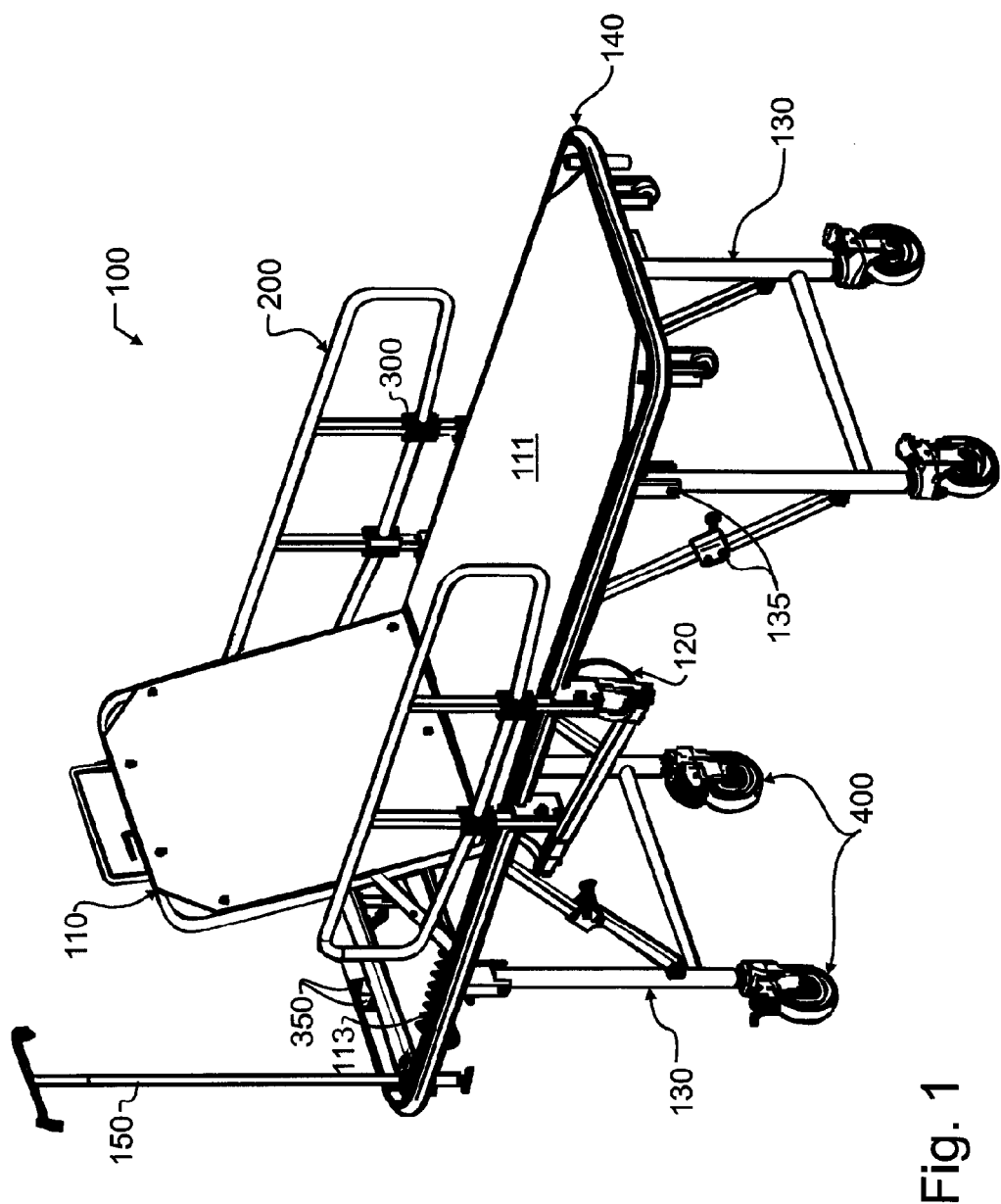
FIG. 1 illustrates a preferred embodiment stretcher compatible with MRI entry systems, designed in accord with the teachings of the present invention, from an isometric projected view.

MRI compatible stretcher 100 is comprised by a Fowler-style back assembly 110 and stretcher main frame 140, each having a patient support surface 111. Optional toothed backrest positioning bracket 113 provides a plurality of positions for back assembly 110, permitting a patient to be raised to a sitting or partially sitting position. An oxygen tank holder 120 is suspended from stretcher main frame 140, and is illustrated with a partial cut-away of c-ring 121 in FIG. 1 for illustrative purposes. A leg assembly 130 which is preferably provided with leg hinges 135 couples stretcher main frame 140 to a set of wheels 400. An auxiliary set of wheels may be provided in fixed relation to stretcher main frame 140 as illustrated in FIG. 1. This combination of leg assemblies 130, leg hinges 135, wheels 400 and auxiliary wheels permits MRI compatible stretcher 100 to be used with ambulances to move a patient between the ambulance floor and street level, and in other applications where it is desirable to accommodate more than one height above an underlying surface. In such application, leg hinges 135 allow leg assemblies 130 to be folded from the position illustrated in FIG. 1 to a collapsed position parallel to the generally planar patient support surface 111. Furthermore, the leg assemblies may be stowed for storage, allowing preferred embodiment MRI compatible stretcher 100 to be stored in a minimum of space. An optional I.V. pole 150 or, in an alternative embodiment, push handles may preferably be adjacent to the head corners of stretcher main frame 140, and other known accessories may be coupled or fitted to preferred embodiment MRI compatible stretcher 100 as will be known in the art.

At a viewing distance such as illustrated by FIG. 1, preferred embodiment MRI compatible stretcher 100 appears to be quite similar to stretchers known in the prior art. However, two additional features are specifically labeled therein. These are electrically insulating and mechanically sound coupling 300 and electrically insulating and mechanically sound coupling 350. These couplings, and similar couplings that may be optionally placed throughout preferred embodiment MRI compatible stretcher 100, drastically alter the behavior of preferred embodiment MRI compatible stretcher 100 in an MRI screening portal or detector.

Figure 2:
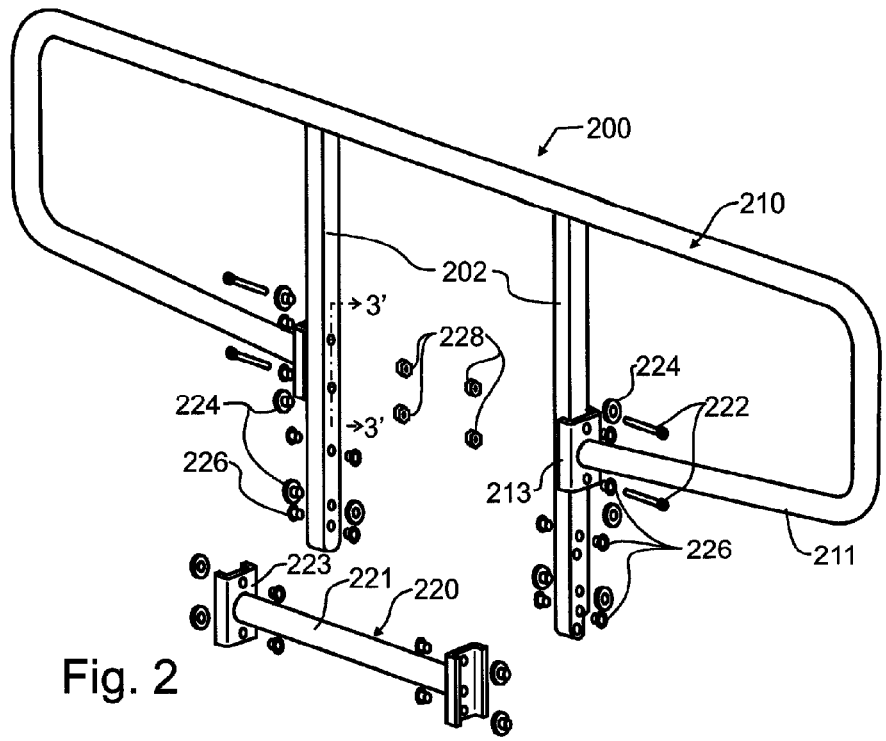
FIG. 2 illustrates a preferred embodiment side guard rail used in the preferred embodiment MRI compatible stretcher of FIG. 1 from an enlarged isometric projected and partially exploded view.

FIG. 2 illustrates a preferred embodiment side guard rail used in the preferred embodiment MRI compatible stretcher, including electrically insulating and mechanically sound coupling 300. A preferred embodiment side rail 200 includes two vertical risers 202, though it will be apparent that the number of such risers is not critical to the present invention. A side rail frame 210 wraps about the vertical risers 202, and has a tubular hand rail 211 terminating at distal ends with a pair of flanges 213. Spanning between these flanges 213 is a side rail center brace 220 that has a longitudinally extensive tubular body member 221 terminating at distal ends in flanges 223.

Figure 3:
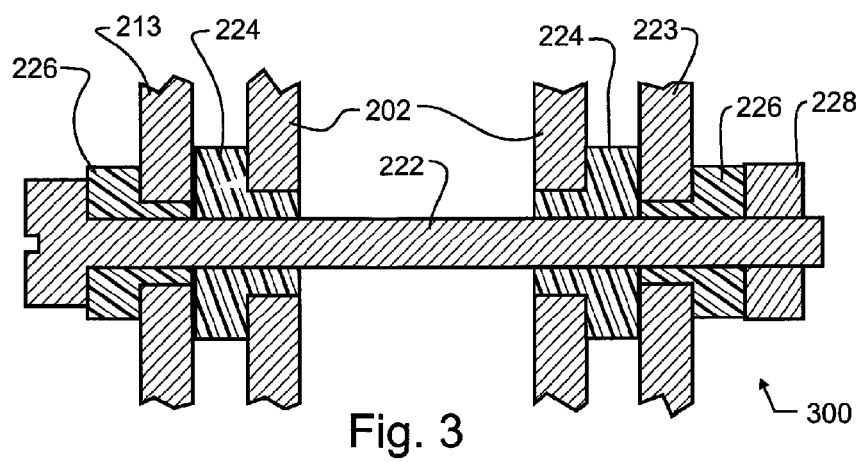
FIG. 3 illustrates a preferred embodiment electrically insulating and mechanically sound coupling used in the preferred embodiment side guard rail of FIG. 2 from a sectional view taken along section line 3' in FIG. 2.

FIG. 3 illustrates the preferred embodiment electrically insulating and mechanically sound coupling 300 in assembled form, from a sectional view taken along section line 3' in FIG. 2. As may be appreciated, bolt 222, which may preferably comprise a metal but non-magnetically susceptible material, serves to fasten the remaining components together. However, a plurality of large electrically non-conductive bushings 224 and small electrically non-conductive bushings 226 isolate bolt 222, locking nut 228, vertical risers 202, flanges 213 and flanges 223 from each other. Consequently, there are no large conductive loops formed, even though at a viewing distance such as illustrated in FIG. 1 the preferred embodiment MRI compatible stretcher 100 appears to be formed with such loops.

Figure 4:
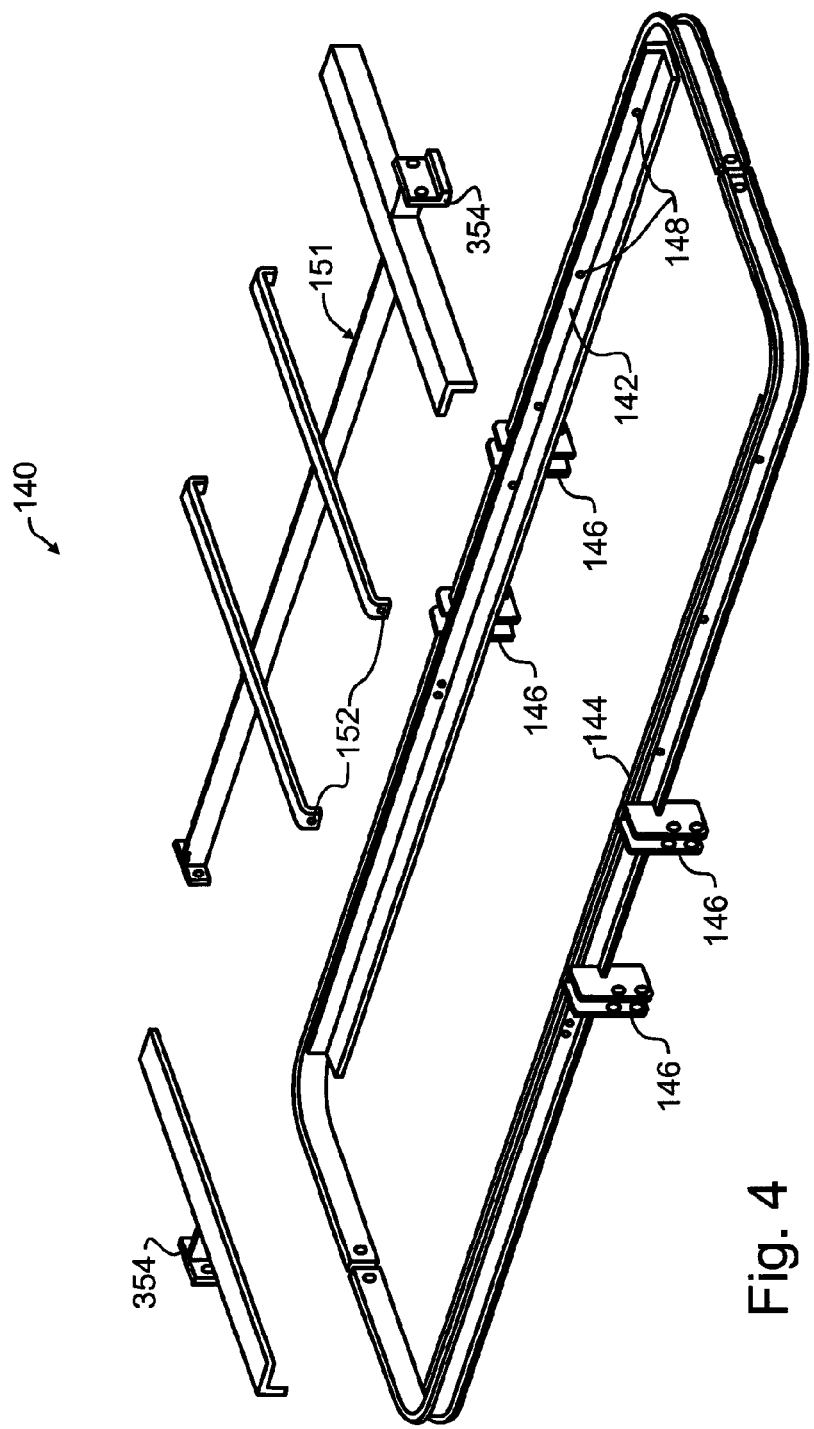
FIG. 4 illustrates a preferred embodiment stretcher main frame used in the preferred embodiment MRI compatible stretcher of FIG. 1 from an isometric projected and partially exploded view.

FIG. 4 illustrates the preferred embodiment stretcher main frame 140 in greater detail, and with obvious or non-critical components removed therefrom for purposes of illustration. Stretcher main frame 140 is divided into two main frame halves 142, 144, which are coupled together at distal ends through cross supports 354. A set of side rail support brackets 146 may optionally be supported by and depend from stretcher main frame 140, and a set of main support coupling holes 148 are provided that in combination with coupling holes 152 permit fasteners to couple main support 151 to main frame halves 142, 144. Most preferably, such fasteners as bolts 222 may be used, and suitable electrically non-conductive bushings 226 will electrically isolate bolts 222, main support 151, and main frame halves 142, 144 from each other, just as metal components are isolated from each other in FIG. 3.

Figure 5:
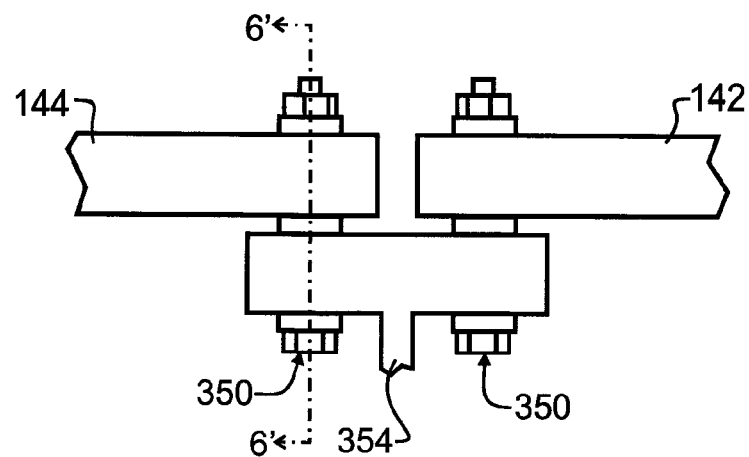
FIG. 5 illustrates a preferred embodiment electrically insulating and mechanically sound coupling used in the preferred embodiment MRI compatible stretcher of FIG. 1 from a top view.
Figure 6:
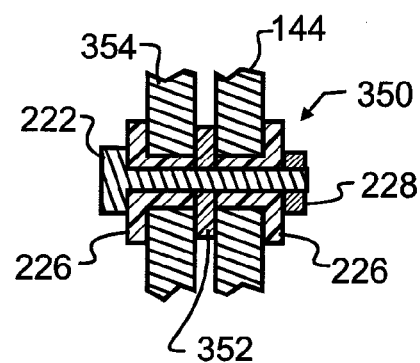
FIG. 6 illustrates the preferred embodiment electrically insulating and mechanically sound coupling of FIG. 5 from a sectional view taken along section line 6' in FIG. 5.

The two main frame halves 142, 144 are coupled together at distal ends through cross supports 354 by electrically insulating and mechanically sound coupling 350 as illustrated in greater detail in FIGS. 5 and 6. A washer 352 in combination with electrically non-conductive bushings 226 will isolate bolt 222 and nut 228 from the two main frame halves 142, 144. However, cross supports 354 span the gap between the two main frame halves 142, 144, providing the strength and mechanical characteristics that would otherwise be intrinsic to a solid and contiguous metal frame. It is this combination of electrical isolation with overlap between adjacent metal parts that is found throughout MRI compatible stretcher 100, and which may be used anywhere within MRI compatible stretcher 100 where a sufficiently large conductive loop may otherwise be formed to trigger an MRI screening portal. This breaking of conductive loops while providing the mechanical characteristics of metals forms the essence of the present invention.

FIG. 7 illustrates a preferred embodiment oxygen tank holder 120 used in preferred embodiment MRI compatible stretcher 100 by partially exploded view. As with prior illustrations, an electrically insulating and mechanically sound coupling incorporating c-ring 121, span bracket 122, washers 352, electrically non-conductive bushings 226, bolts 222 and nuts 228 are arranged when assembled as illustrated in FIG. 8, and together cooperate to provide electrical isolation with overlap between adjacent metal parts. Further, and as visible in FIG. 7, the remaining components of preferred embodiment oxygen tank holder 120 are similarly isolated. So, lower oxygen brace 124 couples to c-rings 121 through a combination of electrically non-conductive bushings 226 and bolts 222 that pass through the longitudinal body of lower oxygen brace 124 and into threaded coupling holes 125 in c-rings 121. Similarly, oxygen connecting brace 128 has a set of electrically non-conductive bushings 226 and bolts 222 that couple to the L-shaped distal termination of lower oxygen brace 124 through a threaded coupling hole 125 formed therein. Finally, connecting brace coupling holes 126, 127 or other suitable fasteners may optionally be provided to permit preferred embodiment oxygen tank holder 120 to be suspended from and coupled with stretcher main frame 140. While not illustrated, it will be understood that there are many different fasteners and means for affixing a tank within c-rings 121. For exemplary purposes only, and not solely limited thereto, bolts may be provided that pass through one or both of c-rings 121 that may be turned to tighten down onto the tank. However, elastomeric rings, gaskets or other fittings or suitable materials may also be provided that secure or affix an oxygen tank within c-rings 121 and oxygen tank holder 120.

FIG. 9 illustrates a preferred embodiment wheel 400 used in preferred embodiment MRI compatible stretcher 100. Wheel 400 may include a ground engaging roller 410 which is preferably fabricated from an electrically non-conductive material such as a polycarbonate plastic or other suitable durable material. A wheel support 420 has a wheel support body 422 also preferably fabricated from an electrically non-conductive material such as a polycarbonate plastic or the like. Wheel support body 422 encompasses and supports ground engaging roller 410. A pin 424, which may be fabricated from aluminum or other similar metal, is retained within wheel support body 422 and provides a pivotal axis for brake 425 to pivot about. A pin 426 similar to pin 424 provides a pivotal axis for wheel lock foot actuator 427 to pivot about. A roller 428 couples wheel lock foot actuator 427 to brake 425. As may be understood, when a person steps on wheel lock foot actuator 427 in the position illustrated in FIG. 9, wheel lock foot actuator 427 will pivot. This in turn will cause roller 428 to push against brake 425, causing brake 425 to pivot down into engagement with ground engaging roller 410, thereby locking wheel 400. The rounded shape of the top surface of brake 425 cooperates with roller 428 to provide two stable positions. The first, illustrated in FIG. 9 is unlocked, while the second, subsequent to a person stepping thereon, is the locked position.

Axle 430, which may also preferably be aluminum, cooperates with aluminum axle nut 432 to hold ground engaging roller 410 within wheel support body 422. Wheel stem 440 may, for exemplary purposes, be coupled to leg assembly 130 using wheel adapter 450 illustrated in FIG. 10. In this case, wheel stem 440 of wheel 400 will pass into stem receiver 454 of cylindrical adapter body 452, and may be threaded, glued, friction fit, or otherwise affixed thereto. A pin hole 456 in wheel adapter 450 will allow a pin to pass through leg assembly 130 and secure wheel adapter 450 therein. Distal to wheel adapter 450, wheel stem 440 will preferably terminate within wheel support body 422, and may, for exemplary purposes, include a large gear having teeth facing downward towards the floor. One or more teeth will preferably protrude upwardly from brake 425 on the end distal to the contact surface that engages with ground engaging roller 410. Preferably then, when a person steps down onto wheel lock foot actuator 427 in the position shown in FIG. 9, causing wheel lock foot actuator 427 to pivot and in turn causing brake 425 to pivot, then as one end of brake 425 comes into contact with ground engaging roller 410, the distal end of brake 425 having one or more upward protruding teeth will simultaneously engage with the large gear terminating wheel stem 440. This allows brake 425 to simultaneously lock wheel 400 against rolling about axle 430 and also against swiveling or pivoting about wheel stem 440. Wheel stem 440 may preferably be provided with a wheel stem coupling 442, which may provide a bearing surface facilitating rotation of wheel stem 440, and which may also be used to secure wheel stem 440 to wheel support body 422.

While the foregoing details what is felt to be the preferred embodiment of the invention, no material limitations to the scope of the claimed invention are intended. Further, features and design alternatives that would be obvious to one of ordinary skill in the art are considered to be incorporated herein. For exemplary purposes only, and not solely limiting thereto, the preferred embodiment has been described using particular materials such as aluminum. However, the present invention is not solely limited thereto, and various other metals, alloys and other suitable materials may be used, as will be apparent from a reading of the present disclosure to those skilled in the art. Similarly, there are many known fasteners that may be substituted for particular fasteners illustrated herein. Consequently, the scope of the invention is not limited solely to the preferred embodiment, and is instead set forth and particularly described in the claims herein below.

We claim:

1. A stretcher compatible with electromagnetic MRI entry screening systems, comprising:
    a stretcher main frame having two electrically conductive main frame members mechanically coupled together through at least one electrically isolated and mechanically coupled electrically conductive cross support, said cross support spanning a gap between said two main frame members;
    a patient support surface supported by said stretcher main frame;
    a side guard having at least one electrically conductive vertical riser, an electrically conductive side rail frame that wraps about said at least one electrically conductive vertical riser having an electrically conductive tubular hand rail terminating at distal ends with a pair of flanges, and spanning between said flanges an electrically conductive side rail center brace that has a longitudinally extensive electrically conductive tubular body member terminating at distal ends in flanges, a plurality of electrically non-conductive bushings electrically isolating said side rail frame flanges from said at least one vertical riser and from said longitudinally extensive electrically conductive tubular body member, a plurality of electrically non-conductive bushings electrically isolating said longitudinally extensive electrically conductive tubular body member flanges from said at least one electrically conductive vertical riser and from said electrically conductive side rail frame, and fasteners securing said side rail frame flanges, said tubular hand rail flanges, said at least one electrically conductive vertical riser, and said electrically non-conductive bushings together;

an oxygen tank holder suspended from said stretcher main frame having an electrically conductive c-ring, an electrically conductive span bracket spanning an open perimeter of said c-ring, electrically non-conductive bushings electrically isolating said span bracket from said c-ring, and fasteners mechanically affixing said span bracket to said c-ring while maintaining electrical isolation between said span bracket and said c-ring;

a set of wheels; and a leg assembly coupling said stretcher main frame to said set of wheels.

2. The stretcher of claim 1, wherein said cross support overlaps each one of said two main frame members adjacent respective distal ends of said cross support to thereby operatively provide a strength characteristic of a solid and contiguous metal frame.

3. The stretcher of claim 1, wherein said span bracket distal ends overlap with said c-ring distal ends to thereby operatively provide a strength characteristic of a solid and contiguous metal ring.

4. The stretcher of claim 1, wherein said main frame members are further comprised by a non-magnetically susceptible composition.

5. The stretcher of claim 1, wherein individual wheels of said set of wheels each further comprise:
  a ground engaging roller fabricated from an electrically non-conductive material;
  a wheel support having a wheel support body fabricated from an electrically non-conductive material;
  a ground engaging roller encompassed and supported by said wheel support body;
  a first pin retained within said wheel support body providing a pivotal axis;
  a brake pivotal about said first pin pivotal axis;
  a second pin providing a pivotal axis;
  a wheel lock foot actuator pivotal about said second pin pivotal axis;
  a roller coupling said wheel lock foot actuator to said brake, and configured when said wheel lock foot actuator pivots to push against and thereby operatively pivot said brake into engagement with said ground engaging roller, thereby locking said wheel; and
  an axle about which said ground engaging roller rolls within said wheel support body.

6. The stretcher of claim 5, further comprising a wheel adapter having a stem receiver, said individual wheels further comprising a wheel stem, individual ones of said wheels' wheel stem coupled to said leg assembly using said wheel stem.

7. The stretcher of claim 6, wherein said wheel adapter further comprises a cylindrical adapter body defining an interior stem receiver into which said wheel stem operatively passes.

8. An electromagnetic MRI entry screening system compatible stretcher, comprising:
  a stretcher main frame having at least two non-magnetically susceptible and electrically conductive main frame member terminations coupled together through at least one electrically isolated and mechanically coupled cross support, said cross support spanning a gap between said at least two non-magnetically susceptible and electrically conductive main frame member terminations and overlapping at distal ends with respective ends of said at least two non-magnetically susceptible and electrically conductive main frame member terminations;
  a patient support surface supported by said stretcher main frame;
  a leg assembly coupling said stretcher main frame to a set of wheels;
  individual wheels of said set of wheels each having a ground engaging roller fabricated from an electrically non-conductive material;
  a wheel support having a wheel support body fabricated from an electrically non-conductive material, said wheel support body encompassing and supporting a ground engaging roller;
  a first pin retained within said wheel support body providing a pivotal axis for a brake to pivot about;
  a second pin providing a pivotal axis for a wheel lock foot actuator to pivot about;
  a roller coupling said wheel lock foot actuator to said brake, and operative when said wheel lock foot actuator pivots to push against and thereby operatively pivot said brake into engagement with said ground engaging roller, thereby locking said wheel, and an axle about which said ground engaging roller rolls within said wheel support body; and
  leg hinges that selectively pivot and thereby operatively allow said leg assembly to fold from generally perpendicular to said stretcher main frame to generally parallel thereto.

9. The electromagnetic MRI entry screening system compatible stretcher of claim 8, further comprising a side guard having:
  at least one non-magnetically susceptible and electrically conductive vertical riser;
  a non-magnetically susceptible and electrically conductive side rail frame that wraps about said at least one vertical riser and having a non-magnetically susceptible and electrically conductive tubular hand rail terminating at distal ends with a pair of flanges; and
  a non-magnetically susceptible and electrically conductive side rail center brace spanning between said hand rail flanges that has a longitudinally extensive tubular body member terminating at distal ends in flanges;
  a plurality of electrically non-conductive bushings electrically isolating said side rail frame flanges from said at least one vertical riser and from said longitudinally extensive tubular body member;
  a plurality of electrically non-conductive bushings electrically isolating said longitudinally extensive tubular body member flanges from said at least one vertical riser and from said side rail frame; and
  fasteners securing said side rail frame flanges, said tubular hand rail flanges, said at least one vertical riser, and said electrically non-conductive bushings together.

10. The electromagnetic MRI entry screening system compatible stretcher of claim 8, further comprising an oxygen tank holder suspended from said stretcher main frame, having:
  a non-magnetically susceptible and electrically conductive c-ring;
  a non-magnetically susceptible and electrically conductive span bracket spanning an open perimeter of said c-ring;

electrically non-conductive bushings electrically isolating said span bracket from said c-ring; and fasteners mechanically affixing said span bracket to said c-ring while operatively preserving electrically isolation between said span bracket and said c-ring.

11. The electromagnetic MRI entry screening system compatible stretcher of claim 10, wherein said span bracket distal ends overlap with said c-ring distal ends to thereby operatively provide a strength characteristic of a solid and contiguous metal ring.

12. The electromagnetic MRI entry screening system compatible stretcher of claim 8, further comprising an auxiliary set of wheels rigidly affixed to said stretcher main frame.

13. The electromagnetic MRI entry screening system compatible stretcher of claim 8, further comprising a wheel adapter having a stem receiver, said individual wheels further comprising a wheel stem, individual ones of said wheels' wheel stem coupled to said leg assembly using said wheel stem.

14. The electromagnetic MRI entry screening system compatible stretcher of claim 13, wherein said wheel adapter further comprises a cylindrical adapter body defining an interior stem receiver into which said wheel stem operatively passes.

15. The electromagnetic MRI entry screening system compatible stretcher of claim 11, wherein said c-ring further comprises:
a first major surface defining an inside perimeter; and
a second major surface defining an outside perimeter; and
wherein said span bracket further comprises a first major surface adjacent to said c-ring second major surface and overlapping therewith.

16. An electromagnetic MRI entry screening system compatible stretcher, comprising:
a stretcher main frame having at least two non-magnetically susceptible and electrically conductive main frame member terminations coupled together through at least one electrically isolated and mechanically coupled cross support, said cross support spanning a gap between said at least two non-magnetically susceptible and electrically conductive main frame member terminations and overlapping at distal ends with respective ends of said at least two non-magnetically susceptible and electrically conductive main frame member terminations;
a patient support surface supported by said stretcher main frame;
first and second electrically non-conductive bushings;
first and second fasteners; and
first and second through holes in said cross support;
each one of said at least two main frame member terminations further comprising a through hole;
said first fastener passing through said first through hole in said cross support, through a first one of said at least two main frame member termination through holes, and through said first electrically non-conductive bushing;

said first electrically non-conductive bushing electrically isolating said first fastener from at least one of said cross support and said at least two main frame member terminations.

17. An electromagnetic MRI entry screening system compatible stretcher, comprising:
a stretcher main frame having at least two non-magnetically susceptible and electrically conductive main frame member terminations coupled together through at least one electrically isolated and mechanically coupled cross support, said cross support spanning a gap between said at least two non-magnetically susceptible and electrically conductive main frame member terminations and overlapping at distal ends with respective ends of said at least two non-magnetically susceptible and electrically conductive main frame member terminations;
a patient support surface supported by said stretcher main frame;
a side guard having:
at least one non-magnetically susceptible and electrically conductive vertical riser;
a non-magnetically susceptible and electrically conductive side rail frame that wraps about said at least one vertical riser and having a non-magnetically susceptible and electrically conductive tubular hand rail terminating at distal ends with a pair of flanges; and
a non-magnetically susceptible and electrically conductive side rail center brace spanning between said hand rail flanges that has a longitudinally extensive tubular body member terminating at distal ends in flanges;
a plurality of electrically non-conductive bushings electrically isolating said side rail frame flanges from said at least one vertical riser and from said longitudinally extensive tubular body member;
a plurality of electrically non-conductive bushings electrically isolating said longitudinally extensive tubular body member flanges from said at least one vertical riser and from said side rail frame; and
fasteners securing said side rail frame flanges, said tubular hand rail flanges, said at least one vertical riser, and said electrically non-conductive bushings together;
an electrically non-conductive bushing;
a fastener;
a through hole in said at least one vertical riser; and
a through hole in a first one of said hand rail flanges;
said fastener passing through said vertical riser through hole, through said hand rail flange through hole, and through said electrically non-conductive bushing;
said electrically non-conductive bushing electrically isolating said fastener from at least one of said vertical riser and said hand rail.

* * * * *